(12) United States Patent
Canady et al.

(10) Patent No.: US 11,004,557 B2
(45) Date of Patent: May 11, 2021

(54) SYSTEM AND METHOD FOR RFID IDENTIFICATION OF ELECTROSURGICAL ACCESSORIES

(71) Applicant: U.S. Patent Innovations, LLC, Takoma Park, MD (US)

(72) Inventors: Jerome Canady, Lakeland, FL (US); Laxmi Ray, Silver Spring, MD (US); Feng Yan, Fairfax, VA (US); Buddika Sumanasena, Silver Spring, MD (US); Taisen Zhuang, Vienna, VA (US)

(73) Assignee: US Patent Innovations, LLC, Takoma Park, MD (US)

( * ) Notice: Subject to any disclaimer, the term of this patent is extended or adjusted under 35 U.S.C. 154(b) by 0 days.

(21) Appl. No.: 16/759,485

(22) PCT Filed: Oct. 10, 2019

(86) PCT No.: PCT/US2019/055584
§ 371 (c)(1),
(2) Date: Apr. 27, 2020

(87) PCT Pub. No.: WO2020/081354
PCT Pub. Date: Apr. 23, 2020

(65) Prior Publication Data
US 2020/0342976 A1 Oct. 29, 2020

Related U.S. Application Data

(60) Provisional application No. 62/746,825, filed on Oct. 17, 2018.

(51) Int. Cl.
*G16H 20/40* (2018.01)
*A61B 34/00* (2016.01)
(Continued)

(52) U.S. Cl.
CPC ......... *G16H 20/40* (2018.01); *A61B 18/1233* (2013.01); *A61B 34/25* (2016.02);
(Continued)

(58) Field of Classification Search
None
See application file for complete search history.

(56) References Cited

U.S. PATENT DOCUMENTS 9,489,785 B2  11/2016  Klammer et al.
10,130,382 B2 * 11/2018  Gladstone .......... A61B 17/1626
(Continued)

*Primary Examiner* — Curtis J King
(74) *Attorney, Agent, or Firm* — 24IP Law Group USA, PLLC; Timothy Dewitt

(57) ABSTRACT

A method for authenticating an electrosurgical system accessory comprising initiating a surgical procedure through a user interface on an electrosurgical generator, automatically determining whether an electrosurgical accessory is plugged into a generator receptacle, activating an RFID reader connected to the generator in response to a determination that an accessory is plugged into a receptacle, transmitting through the RFID reader to an RFID tag in the accessory a privacy password, transmitting a unit identification code from the RFID tag to the generator, displaying a device type associated with the transmitted unit identification code, checking a status of the accessory, unlocking a tag memory management if the read status code indicates the accessory has not previously been used, reading encoded data from the tag memory, computing a device authentication code from tag memory encoded data, transmitting the computed authentication code to the tag, and enabling the accessory in response to a match.

11 Claims, 10 Drawing Sheets

(51) Int. Cl.
*A61B 90/98* (2016.01)
*G16H 40/63* (2018.01)
*A61B 18/12* (2006.01)
*G06F 21/31* (2013.01)
*G06K 7/10* (2006.01)
*A61B 18/04* (2006.01)
*A61B 18/00* (2006.01)
*A61M 13/00* (2006.01)

(52) U.S. Cl.
CPC .............. *A61B 90/98* (2016.02); *G06F 21/31* (2013.01); *G06K 7/10366* (2013.01); *G16H 40/63* (2018.01); *A61B 18/042* (2013.01); *A61B 2018/00178* (2013.01); *A61B 2018/00988* (2013.01); *A61M 13/003* (2013.01)

(56) References Cited

U.S. PATENT DOCUMENTS

| | | | |
|---|---|---|---|
| 2001/0020148 A1 | 9/2001 | Sasse et al. | |
| 2003/0231990 A1 | 12/2003 | Faries et al. | |
| 2006/0129140 A1* | 6/2006 | Todd | G06K 17/00 606/1 |
| 2007/0027459 A1* | 2/2007 | Horvath | G16H 40/40 606/147 |
| 2008/0020714 A1* | 1/2008 | Mezhinsky | A61B 90/92 455/73 |
| 2008/0200844 A1* | 8/2008 | Millahn | A61B 90/90 600/595 |
| 2010/0026456 A1* | 2/2010 | Cline | G06K 7/10316 340/10.1 |
| 2010/0079001 A1* | 4/2010 | Lee | H01R 25/003 307/40 |
| 2010/0185048 A1* | 7/2010 | Lonky | A61M 1/0031 600/37 |
| 2010/0252626 A1* | 10/2010 | Elizondo | G06Q 10/087 235/385 |
| 2013/0231656 A1* | 9/2013 | Dunning | A61B 90/90 606/34 |
| 2014/0128885 A1* | 5/2014 | Dachs, II | A61B 90/98 606/130 |
| 2014/0180272 A1* | 6/2014 | Dachs, II | A61B 18/14 606/34 |
| 2014/0276547 A1* | 9/2014 | Lonky | A61M 1/0066 604/503 |
| 2015/0150546 A1* | 6/2015 | Goldschmidt | A61B 90/98 606/1 |
| 2015/0351822 A1* | 12/2015 | Mulcahey | A61B 18/0218 606/22 |
| 2016/0045365 A1* | 2/2016 | Foster | A61B 90/96 285/124.1 |
| 2016/0055359 A1 | 2/2016 | Jensen et al. | |
| 2016/0371574 A1* | 12/2016 | Nguyen | G06K 17/0022 |
| 2017/0032306 A1 | 2/2017 | Johnson et al. | |
| 2017/0312044 A1* | 11/2017 | Conlon | A61B 17/320092 |
| 2018/0026795 A1* | 1/2018 | Klammer | H04L 63/083 713/176 |
| 2019/0110862 A1* | 4/2019 | Anderson | A61B 90/96 |
| 2019/0388137 A1* | 12/2019 | Henrywood | A61B 90/98 |
| 2020/0078113 A1* | 3/2020 | Sawhney | G06F 3/0481 |
| 2020/0106220 A1* | 4/2020 | Henderson | A61B 18/1206 |
| 2020/0237398 A1* | 7/2020 | Groene | A61B 17/320092 |

\* cited by examiner

SYSTEM AND METHOD FOR RFID IDENTIFICATION OF ELECTROSURGICAL ACCESSORIES

CROSS-REFERENCE TO RELATED APPLICATIONS

The present application claims the benefit of the filing date of U.S. Provisional Patent Application Ser. No. 62/746,825 filed by the present inventors on Oct. 17, 2018.

The aforementioned provisional patent application is hereby incorporated by reference in its entirety.

STATEMENT REGARDING FEDERALLY SPONSORED RESEARCH OR DEVELOPMENT

None.

BACKGROUND OF THE INVENTION

Field of the Invention

The present invention relates to electrosurgical systems, and more particularly, to a system and method for automatic identification of attachments for an electrosurgical system, authentication and one time use of company brand line surgical devices/accessories for an electrosurgical system.

Brief Description of the Related Art

A variety of systems and methods for automatic identification of accessories for electrosurgical systems and have been developed. One type of such systems and methods is radio frequency (RFID) identification. In an RFID system, an RFID tag or transponder is physically attached or embedded in the electrosurgical attachment. An RFID reader is then used to wirelessly read data stored in the RFID tag and/or write information to the RFID tag in the accessory. Typically, an RFID tag has an RF antenna and an integrated circuit. The RF antenna both receives power and data from the reader and is used to transmit data from the tag to the reader. The integrated circuit typically has a processor for processing data and for modulating and demodulating the RF signal, and a memory for storing data. An RFID tag can be read-only or can be read-write such that at least some of the data in the memory on the tag can be altered or deleted.

Certain types or models of read-write RFID tags—herein called secure RFID tags —provide security or protection features or mechanisms, such that reading and/or writing of the tag is controlled and conditioned upon successful communication of one or more passwords. In these secure RFID tags, a password is stored in write-only storage; that is, a password can be set or changed by a write operation but cannot be revealed by any read operation. For a reader to gain access to data in the secure RFID tag, any read or write operations must be preceded by a password operation, in which the tag compares the interrogator's offered password to the tag's stored password. The secure RFID tag normally indicates success or failure of password comparison in its response to the password operation. Successful matching of passwords will temporarily enable subsequent read or write operations, until the tag is reset, either deliberately by the interrogator (at the end of operations), or incidentally by loss of power when a passive tag is removed from the vicinity of the interrogator.

An RFID tag may be employed for a variety of purposes. One such purpose is to authenticate an accessory device (e.g., a surgical instrument) to determine whether the accessory or instrument device is suitable for use with a main device, (e.g., an electrosurgical or microwave generator). Authentication is prepared or provisioned by generating and storing—or "programming"—a secret piece of information in the tag which is attached or affixed to the accessory device. This secret, called an "authentication signature," is intended to be known or determinable only by the programmer of the RFID tag and by the manufacturer, vendor, or owner of the main and accessory devices to be authenticated. In subsequent usage intended to be protected by authentication, the authentication signature must be communicated between the interrogator and the secure RFID tag for comparison. Secure RFID tags can perform encryption or decryption if an authentication code/signature is transmitted as password. An encrypted password is transmitted between reader and tag, which is decrypted by the tag to calculate actual password transmitted from the reader. Nevertheless, if the authentication signature is stored or written in the user memory of the tag, the authentication signature can be exposed by RF communication in plaintext during authentication events. Thus, an adversary may attempt to discover authentication signatures with readily-available apparatus, such as RFID interrogators, and RF signal capture or recording devices ("sniffers").

If the authentication signature were a simple secret (key or password) shared in common by all instances of accessory devices within a population of devices, any discovery by an adversary—no matter by what means—of one authentication signature would break authentication for an unlimited number of accessory devices.

In prior art systems, the authentication signature is stored in a known location in read-write memory in the RFID tag. In these systems, a main device seeking to authenticate an accessory will read the UID from the RFID tag associated with the accessory, and perform an identical calculation using the same secret key as that which presumably was used to program the tag initially. The stored authentication signature is then read from the RFID tag of the accessory and compared to the calculated authentication signature. If a match is confirmed, the accessory is judged to be authentic.

Such prior-art systems have disadvantages because they require consumption of read-write memory which is a scarce resource in an RFID tag; and because RFID read-write memory, may be accessible by any party in possession of an easily obtainable RFID interrogator, and thus the authentication signature for a given RFID chip may be readily readable. Another disadvantage of such readability is that an adversary who can read some number of authentication signatures may be able to deduce or derive the pattern or rule of diversification for a large population of accessory devices, and thus defeat the authentication system.

Another RFID identification for accessories to electrosurgical systems is disclose din U.S. Pat. No. 9,489,785, which is directed to a secure RFID authentication system, apparatus, and related methods of use. Memory areas of the RFID tag that are normally associated with password functions are adapted to store an authentication signature, thereby freeing read-write memory to be allocated for application usage. In some embodiments, an RFID tag includes password-controlled access to read and/or write functions. By storing the authentication signature as a read, write, read-write, or other password, the ability to read, write, or further operate or communicate with an RFID tag can be prevented and therefore, the use of devices associated with such tags may also be controlled more reliably and securely. For example, and without limitation, RFID tags in accordance with the present disclosure may be utilized to control interoperability of devices, to enable the use of authentic devices and/or accessories and to disallow the use of unauthorized devices and/or accessories, with greater certainty and reliability than with prior-art approaches that are vulnerable to attack and compromise.

SUMMARY OF THE INVENTION

In a preferred embodiment, the present invention is a method for authentication an accessory for an electrosurgical system comprising the steps of initiating a surgical procedure through a user interface on an electrosurgical generator, automatically determining whether an electrosurgical accessory is plugged into a receptacle in the electrosurgical generator, activating an RFID reader connected to the electrosurgical generator in response to a determination that an accessory is plugged into a receptacle in the electrosurgical generator, transmitting from the generator through the RFID reader to the tag a privacy password, transmitting a unit identification code from the RFID tag through the reader to the generator, displaying on a display in the generator a device type associated with the transmitted unit identification code, checking a status of the accessory by reading a status code from memory in the tag, displaying a warning if a read status code from the tag memory indicates that the accessory previously has been used, unlocking a tag memory management if the read status code indicates the accessory has not previously been used, reading encoded data from the tag memory, computing in the generator a device authentication code from tag memory encoded data, transmitting the computed authentication code from the generator to the tag, and enabling the accessory in response to a match between the computed authentication code and a tag authentication code stored in memory in the tag. The method further may comprises wirelessly making changes in the RFID tag memory to indicate that the accessory has been used. Still further, the method may comprise permanently disabling (or "killing") the RFID tag in the accessory wirelessly if a user attempts to re-use already used disposable surgical devices even after a displayed warning upon detection of a used in an accessory tag. After the accessory is enabled, the system may display on the user interface a message indicating the accessory is accepted for use.

Even further, in response to the unlocking of the RFID tag memory management, the method may include reading encoded data from the RFID tag memory, the encoded data comprising data indicative of at least one of an accessory manufacture date and an accessory expiration date, comparing with a processor or CPU in the electrosurgical generator the at least one of an accessory manufacture date and an accessory expiration date to real-time data to determine if the accessory is expired, if the accessory is expired, displaying an expired message on a display; and if the accessory is not expired, proceeding to the step of reading encoded data from the RFID tag memory.

In an alternative embodiment, the present invention is a method for authentication of an accessory for an electrosurgical system. The method comprises automatically determining whether an electrosurgical accessory is plugged into a receptacle in the electrosurgical generator, transmitting from the generator through an RFID reader to an RFID tag in the accessory a privacy password in response to the accessory being detected at plugged into a receptable in the electrosurgical generator, checking a status of the accessory by reading a status code from memory in the RFID tag, displaying a warning on a display in the electrosurgical generator if a read status code from the tag memory indicates that the accessory previously has been used, unlocking memory management of the RFID tag memory if the read status code indicates the accessory has not previously been used, reading encoded data from the RFID tag memory, computing in the electrosurgical generator a device authentication code from the encoded data read from the RFID tag memory, transmitting the computed authentication code from the electrosurgical generator to the RFID tag; and enabling the accessory in response to a match between the computed authentication code and an RFID tag authentication code stored in memory in the RFID tag. The method may further comprise transmitting a unit identification code from the RFID tag through the RFID reader to the electrosurgical generator, displaying on a display in the electrosurgical generator a device type associated with the transmitted unit identification code, and determining with a processor or CPU in the electrosurgical generator whether a device type associated with the unit identification code is compatible with a surgical procedure selected on a graphical user interface associated with the electrosurgical generator.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description or may be learned by practice of the invention.

BRIEF DESCRIPTION OF THE DRAWINGS

For a more complete understanding of the present invention and the advantages thereof, reference is now made to the following description and the accompanying drawings, in which.

DETAILED DESCRIPTION OF THE PREFERRED EMBODIMENTS

Figure 1A:
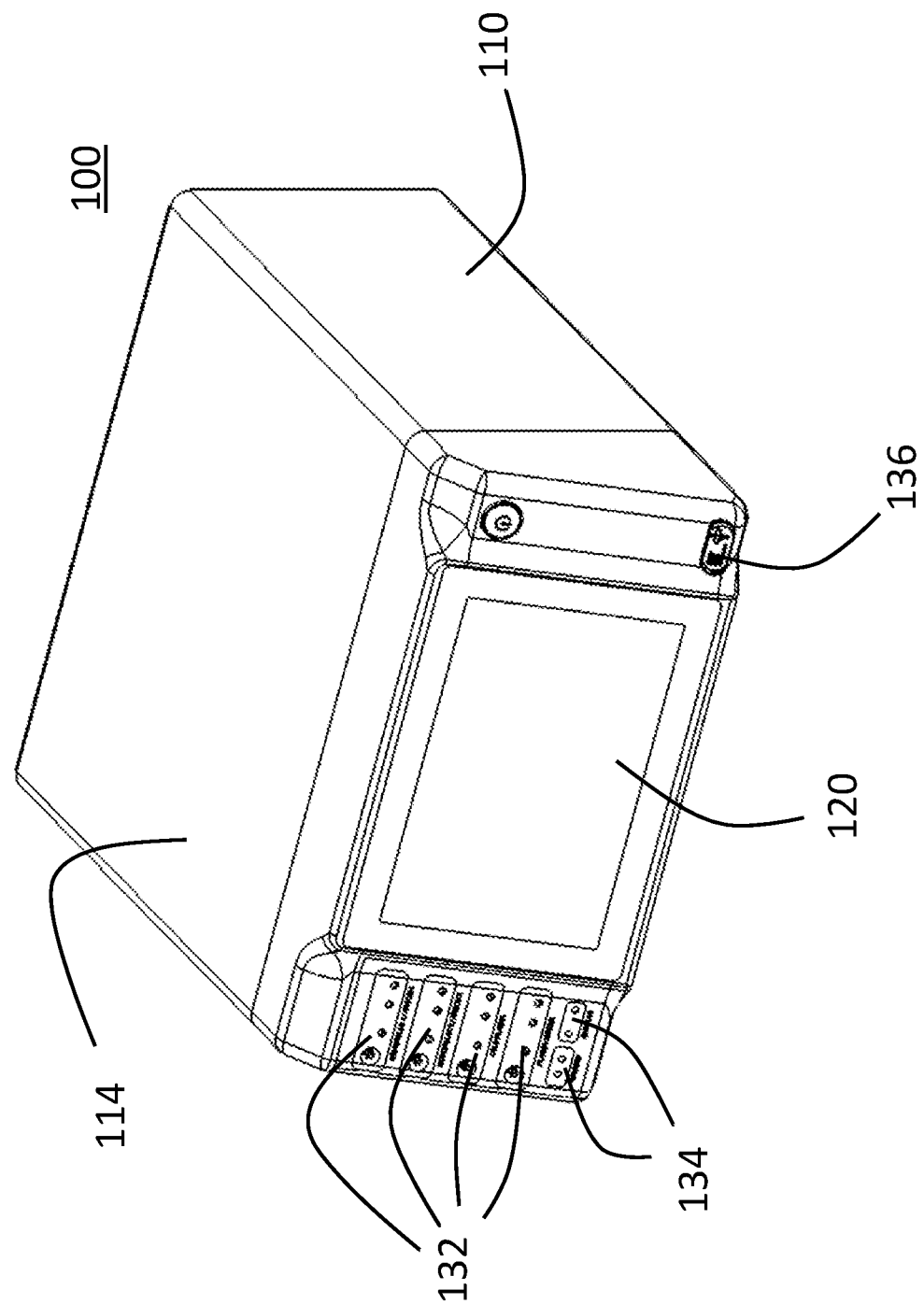
FIG. 1A is a perspective view of a preferred embodiment of a gas-enhanced electrosurgical generator.
Figure 1B:
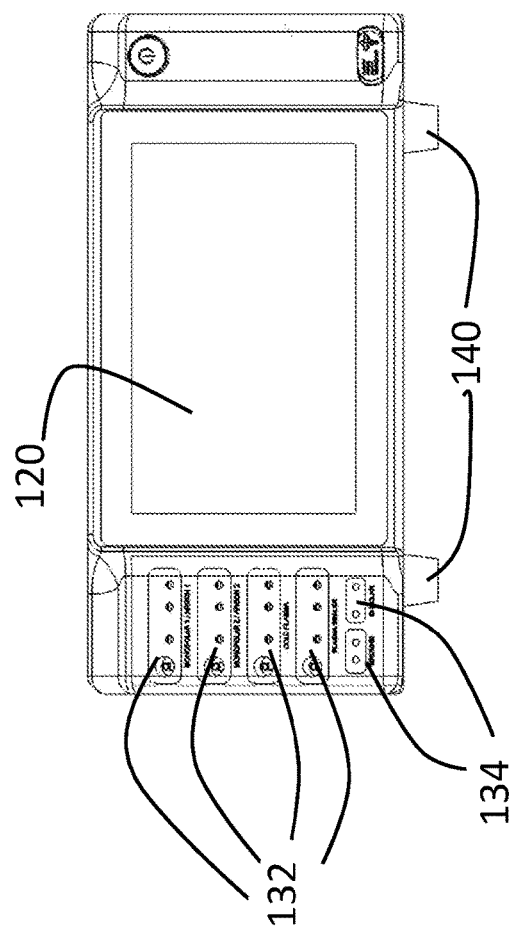
FIG. 1B is a front view of a preferred embodiment of a gas-enhanced electrosurgical generator.
Figure 1C:
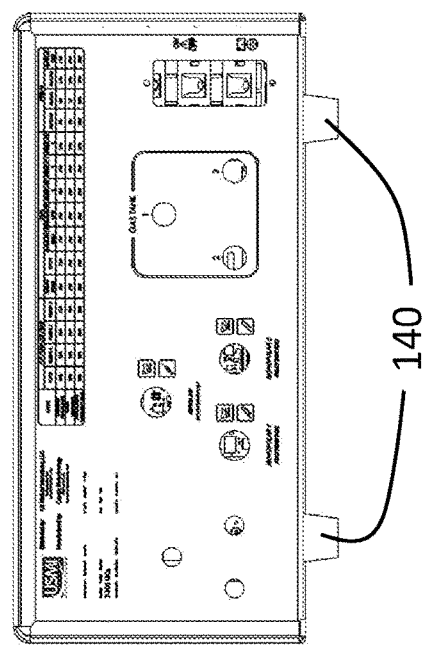
FIG. 1C is a rear view of a preferred embodiment of a gas-enhanced electrosurgical generator.
Figure 1D:
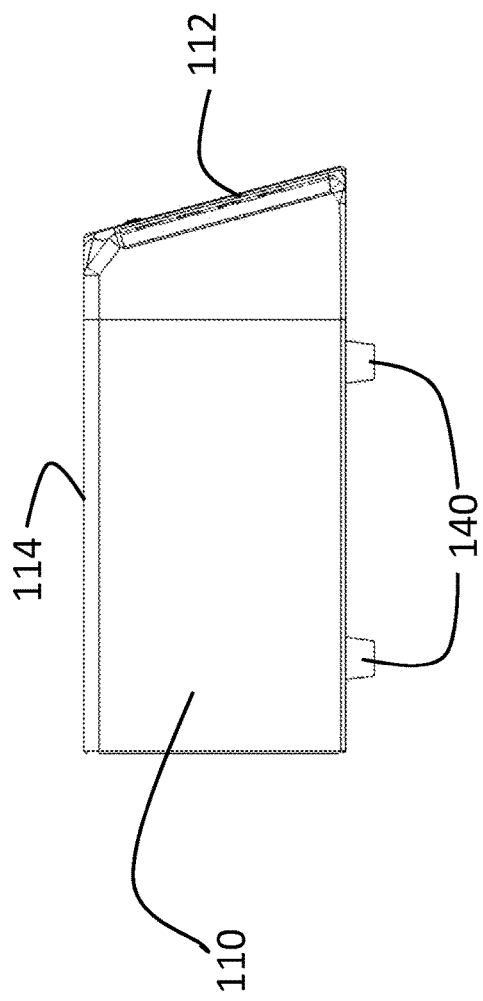
FIG. 1D is a left side view of a preferred embodiment of a gas-enhanced electrosurgical generator.
Figure 1E:
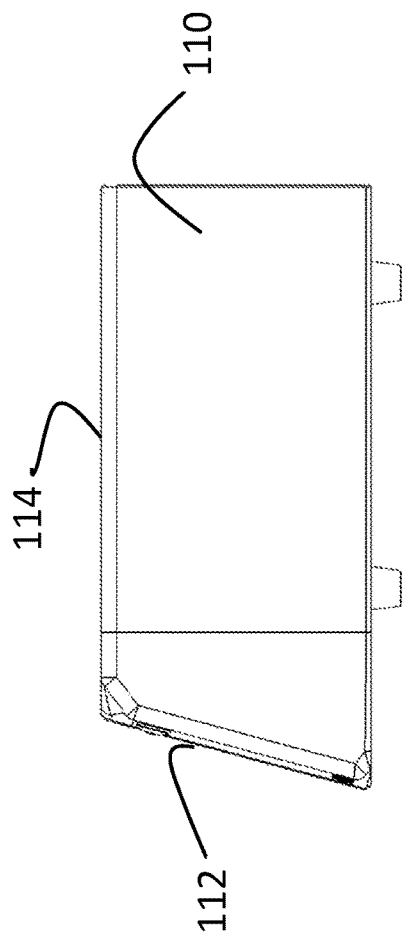
FIG. 1E is a right view of a preferred embodiment of a gas-enhanced electrosurgical generator.
Figure 1G:
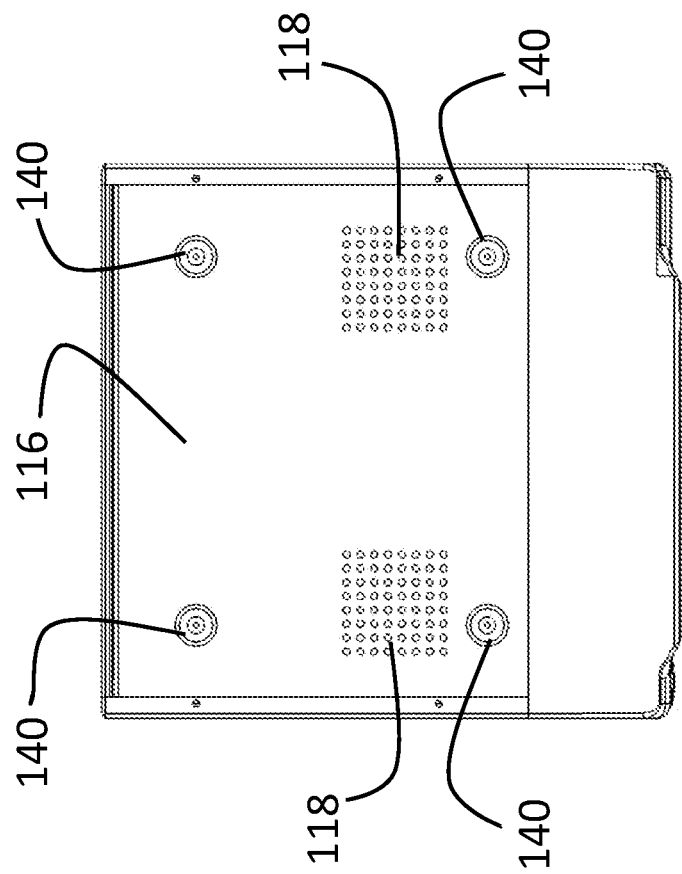
FIG. 1G is a bottom view of a preferred embodiment of a gas-enhanced electrosurgical generator.
Figure 1F:
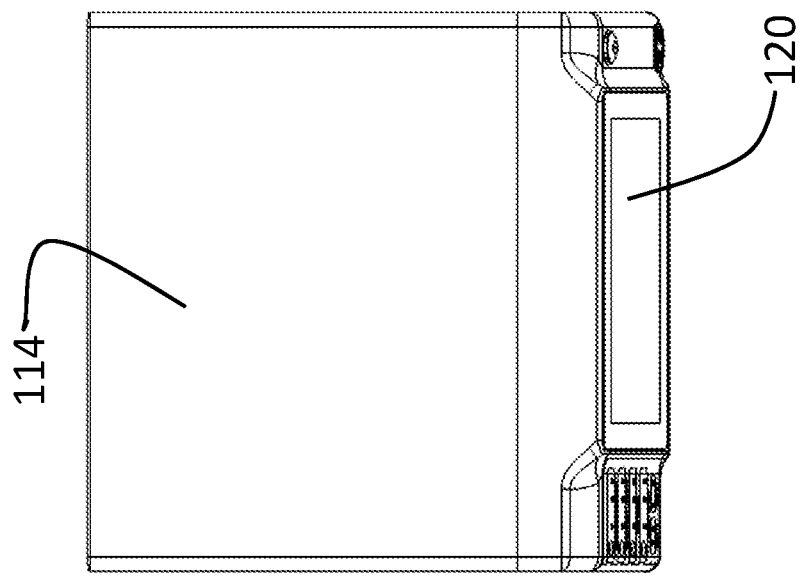
FIG. 1F is a top view of a preferred embodiment of a gas-enhanced electrosurgical generator.

The systems and methods of the present invention may be used, for example, with an electrosurgical system such as is disclosed in PCT/US2018/026892, which is hereby incorporated by reference. In that system, a gas-enhanced electrosurgical generator 100 is shown in FIGS. 1A-1G. The gas-enhanced generator has a housing 110 made of a sturdy material such as plastic or metal similar to materials used for housings of conventional electrosurgical generators. The housing 110 has a removable cover 114. The housing 110 and cover 114 have means, such as screws 119, tongue and groove, or other structure for removably securing the cover to the housing. The cover 114 may comprise just the top of the housing or multiple sides, such as the top, right side and left side, of the housing 110. The housing 110 may have a plurality of feet or legs 140 attached to the bottom of the housing. The bottom 116 of the housing 110 may have a plurality of vents 118 for venting from the interior of the gas-enhanced generator.

On the face 112 of the housing 114 there is a touch-screen display 120 and a plurality of connectors 132, 134 for connecting various accessories to the generator, such as an argon plasma probe, a hybrid plasma probe, a cold atmospheric plasma probe, or any other electrosurgical attachment. There is a gas connector 136 for connecting, for example, a $CO_2$ supply for insufflating an abdomen. The face 112 of the housing 110 is at an angle other than 90 degrees with respect to the top and bottom of the housing 110 to provide for easier viewing and use of the touch screen display 120 by a user.

Figure 2A:
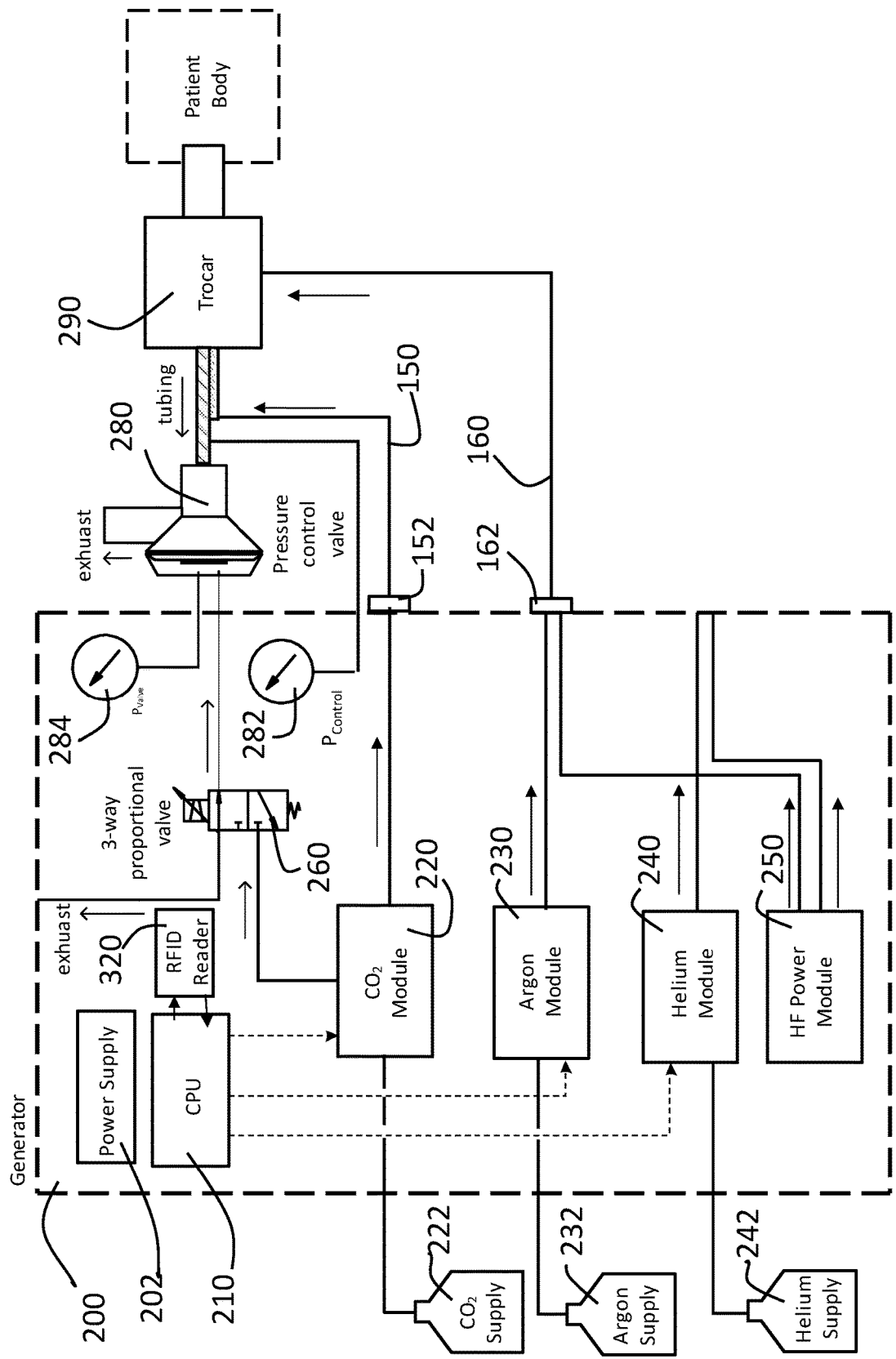
FIG. 2A is a block diagram of a preferred embodiment of pressure control system of a gas-enhanced electrosurgical generator in accordance with the present invention configured to perform an argon-enhanced electrosurgical procedure.

One or more of the gas control modules may be mounting within a gas-enhanced electrosurgical generator 100. A gas pressure control system 200 for controlling a plurality of gas control modules 220, 230, 240 within a gas-enhanced electrosurgical generator is described with reference to FIGS. 2A-2B. A plurality of gas supplies 222, 232, 242 are connected to the gas pressure control system 200, and more specifically, to the respective gas control modules 220, 230, 240 within the gas pressure control system 200. The gas pressure control system 200 has a power supply 202 for supplying power to the various components of the system. A CPU 210 controls the gas pressure control modules 220, 230, 240 in accordance with settings or instructions entered into the system through a graphical user interface on the display 120. The system is shown with gas control modules for $CO_2$, argon and helium, but the system is not limited to those particular gases. In the embodiment shown in FIGS. 2A-2B, the $CO_2$ is shown as the gas used to insufflate an abdomen (or other area of a patient). The gas pressure control system 200 has a 3-way proportional valve connected to the gas control module 220. While FIG. 2A shows the 3-way proportional valve connected only to the CO2 control module 220, the 3-way proportional valves could be connected to a different gas control module 230 or 240. The gas pressure control system 200 further has an HF power module 250 for supplying high frequency electrical energy for various types of electrosurgical procedures. The HF power module contains conventional electronics such as are known for provide HF power in electrosurgical generators. Exemplary systems include, but are not limited to, those disclosed in U.S. Pat. Nos. 4,040,426 and 4,781,175. The system further could have a converter unit for converting the HF power to a lower frequency, such as may be used for cold atmospheric plasma and is described in U.S. Patent Application Publication No. 2015/0342663.

Figure 2B:
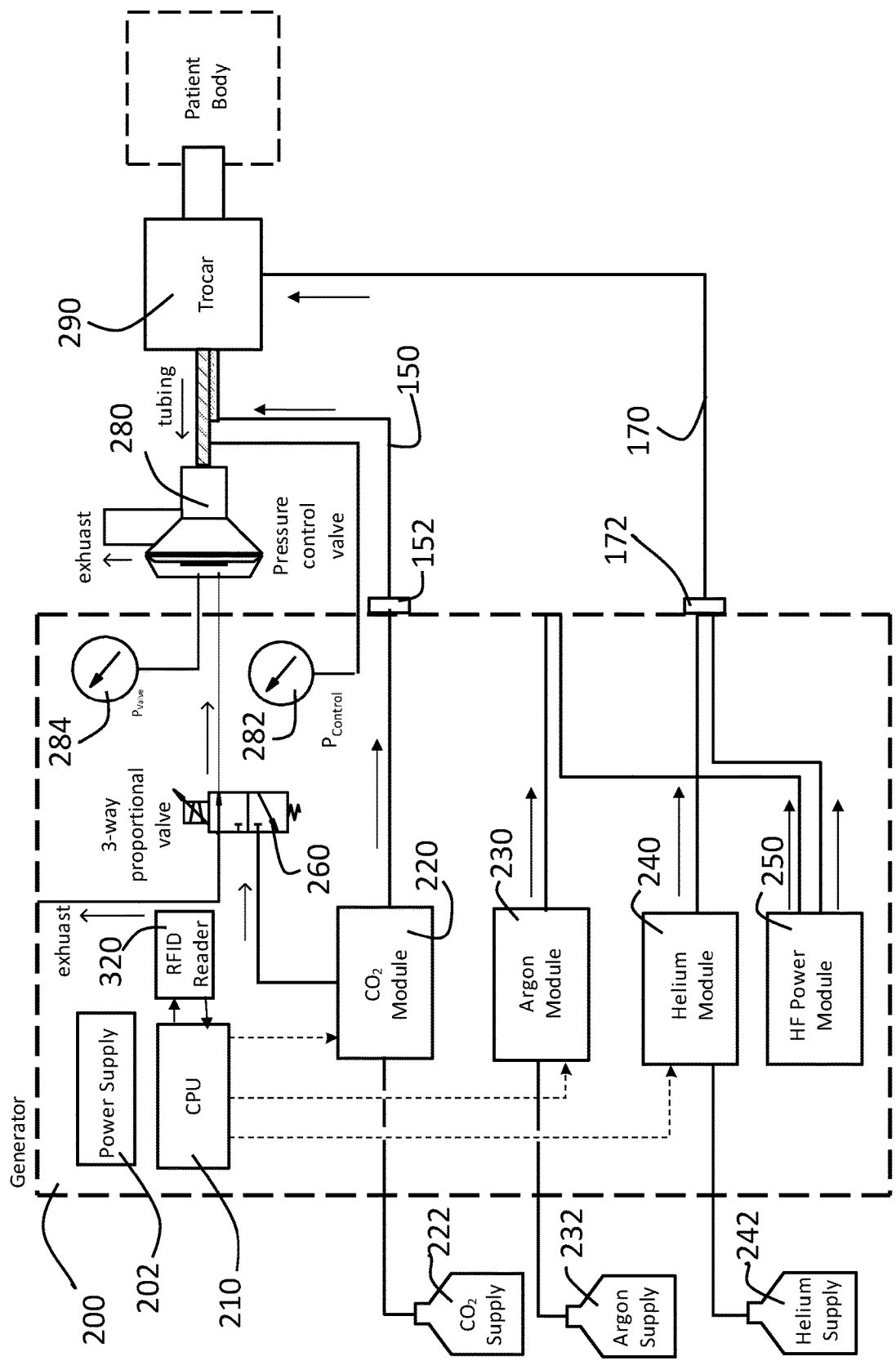
FIG. 2B is a block diagram of a preferred embodiment of pressure control system of a gas-enhanced electrosurgical generator in accordance with the present invention configured to perform a cold atmospheric plasma procedure.

The outlet port of gas control module 220 is connected to a connector 136 on the generator housing. While connector 136 and the other connectors are shown on the front face of the housing 110, they could be elsewhere on the housing. The outlet ports of gas control modules 230, 240 each are connected to tubing or other channel to a connector. As shown in FIG. 2A the connector 132 to which control module 230 is connected has a gas-enhanced electrosurgical instrument 160 having a connector 162 connected to in. In FIG. 2A, gas control module 230 controls flow of argon gas, so the instrument 160 is an argon gas-enhanced electrosurgical tool such as an argon plasma probe such as is disclosed in U.S. Pat. No. 5,720,745, a hybrid plasma cut accessory such as is disclosed in U.S. Patent Application Publication No. 2017/0312003 or U.S. Patent Application Publication No. 2013/0296846, or a monopolar sealer such as is disclosed in U.S. Patent Application Publication No. 2016/0235462. Other types of argon surgical devices similarly can be used. As shown in FIG. 2B the connector 132 to which control module 240 is connected has a gas-enhanced electrosurgical instrument 170 having a connector 172 connected to in. In FIG. 2B, gas control module 240 controls flow of helium gas, so the instrument 170 is, for example, a cold atmospheric plasma attachment such as is disclosed in U.S. Patent Application Publication No. 2016/0095644.

The system provides for control of intraabdominal pressure in a patient. The pressure control valve 280 has a chamber within it. The pressure in that chamber is measured by pressure sensor 284. $CO_2$ is supplied to the chamber within pressure control valve 280 from gas control module 220 via 3-way proportional valve 260. Pressure in that chamber within the pressure control valve 280 also may be released via 3-way proportional valve 260. In this manner, the system can use the pressure sensor 284 and the 3-way proportional valve to achieve a desired pressure (set through a user interface) in the chamber within the pressure control valve 280. The pressure sensor 282 senses the pressure in the tubing (and hence the intraabdominal pressure). The pressure control valve 280 then releases pressure through its exhaust to synchronize the intraabdominal pressure read by sensor 282 with the pressure in the chamber within the pressure control valve as read by pressure sensor 284. The readings from sensors 282, 284 can be provided to CPU 210, which in turn can control flow of $CO_2$ and one of argon and helium, depending on the procedure being performed, to achieve a stable desired intraabdominal pressure.

Figure 3:
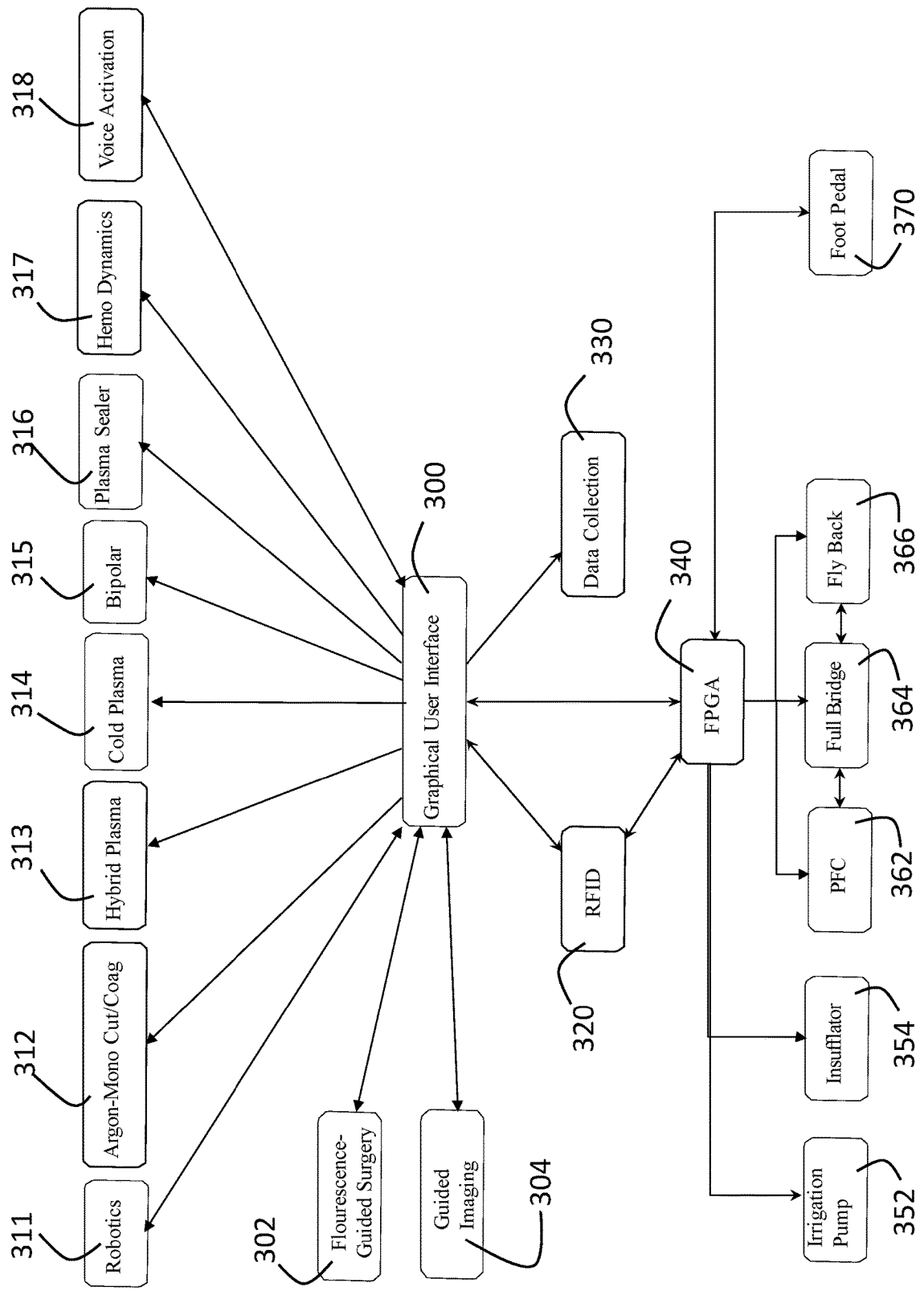
FIG. 3 is a diagram of a graphical user interface in accordance with a preferred embodiment of the present invention.

As shown in FIG. 3, the generator further may have graphical user interface 300 for controlling the components of the system using the touch screen display 120. The graphical user interface 300 for example, may control robotics 311, argon-monopolar cut/coag 312, hybrid plasma cut 313, cold atmospheric plasma 314, bipolar 315, plasma sealer 316, hemo dynamics 317 or voice activation 318. The graphical user interface further may be used with fluorescence-guided surgery 302. For example, J. Elliott, et al., "Review of fluorescence guided surgery visualization and overlay techniques," BIOMEDICAL OPTICS EXPRESS 3765 (2015), outlines five practical suggestions for display orientation, color map, transparency/alpha function, dynamic range compression and color perception check. Another example of a discussion of fluorescence-guided surgery is K. Tipirneni, et al., "Oncologic Procedures Amenable to Fluorescence-guided Surgery," Annals of Surgery, Vo. 266, No. 1, July 2017). The graphical user interface (GUI) further may be used with guided imaging such as CT, MM or ultrasound. The graphical user interface may communicate with peripheral or accessory devices through RFID reader 320 (such as may be found in various electrosurgical attachments) and may collect and store usage data 330 in a storage medium. The RFID reader may be in the generator as shown in FIGS. 2A and 2B or may be attached to the generator and in communication with the CPU in the generator. The graphical user interface 300 communicates with FPGA 340, which may control irrigation pump 352, insufflator 354, PFC 362, full bridge 364 for adjusting the power output, fly back 366 for regulating the power (DC to AC) and a foot pedal 370.

The operation of the RFID system is described with reference to FIGS. 4A and 4B. GUI on the generator touch screen provides touch screen buttons to start or initiate device identification process. During manufacture, devices will be assigned unique device identification codes which will be read wirelessly by the reader and sent to processor or CPU of the electrosurgical generator for display in GUI. RFID system tracks device identification code encoded in the tag internal memory. RFID tags will be embedded in all surgical accessories.

Alternatively, a user may enter into the graphical user interface in the electrosurgical generator the accessory that is going to be used (402). This can be done via a button list on the touch screen, by typing in a device identifier through a keyboard displayed on the touch screen or on a keyboard or other input device attached (wired or wireless) to the generator's graphical user interface. Alternative, a user may select a particular surgical procedure on the graphical user interface and a processor or CPU in the electrosurgical generator can determine the selection an acceptable accessory for the selected procedure.

A processor or CPU in the electrosurgical generator checks an electronic switch, button, sensor or signal in the accessory receptacle on the generator to determine whether a device is plugged into the receptacle (404). At this step, the processor or CPU may be checking whether a signal was received from any of a plurality of receptacles or may check only the receptacle appropriate for the device type entered at step 402. If no device is found to be plugged in the processor or CPU stops the process (406) and a message is played on the touch screen (408) or the user is notified by some other means such as a sound or alarm indicating that no accessory is attached.

If an accessory is found to be attached to the generator at step 404, the RFID reader 320 in or attached to the generator is activated (405) and pairs with an RFID tag in the accessory. The RFID reader 320 has two-way communication with the CPU210. The pairing may or may not include powering up the tag depending on whether the RFID tag has a battery. Once the RFID reader 320 and tag are paired, the reader unlocks the tag privacy mode by transmitting a privacy password (410).

The RFID reader 320 then retrieves a unit identifier (UID) and device classification code from the tag (412) and may display on the generator touch screen or other display a device type corresponding to the retrieved code (413). For example, the device type can be monopolar, endo-probe, bipolar, cold plasma, argon plasma, hybrid plasma or other type. Additionally, a processor or CPU in the electrosurgical generator may determine, for example via accessing a stored database, whether a device type associated with the device classification code is acceptable for a surgical procedure selected through the graphical user interface. Again, a responsive message may be displayed on the display indicating a result of such determination.

The RFID reader 320 then checks the device status (first-time use/non-first-time use) by tracing a secret code encoded in the tag. (420). If it the status is not first-time use, use of the accessory is disabled (422) and an access denied or stop message is displayed (414) on the touch screen or other display or an audible signal is given to indicate to the user that the accessory previously has been used (424).

If it is a first-time use of the device, the RFID reader unlocks the tag memory with 64-bit user memory password protection (430). Encoded data regarding the accessory is then read from the tag by the reader and provided to a processor or CPU in the generator (432). The processor or CPU then computes a device authentication code from user memory encoded data and an algorithm for authentication code generation (434). The authentication code is then transmitted from the RFID reader to the tag as an encrypted password (436).

The processor in the tag then checks if there is a password match between the transmitted password and the password encoded in the tag (440). If there is not a match, the device is disabled (442) and a message is displayed on the touch screen (444) that the device has not been identified as a genuine device.

If the device is found to be genuine (450), the device is accepted by the system and a message reflecting that acceptance is displayed on the touch screen (452). The system then marks the accessory as used by making a modification in the password protected secret code so the device cannot later be re-used (454). The system will then transmit a privacy password to the tag to enable privacy mode (456). At this point, the system will shut down the RFID reader function (458).

The plugged in authenticated accessory device now is valid for cut/coag/power delivery as per user setting on the generator (460). The FPGA continuously monitors the authenticated devices plugged-in status (462). If the device is unplugged, the FPGA controller causes the system to cut off power delivery.

The system monitors or checks whether there is any further input from a user to re-activate the RFID reader (470). If there is further user input and the surgical process is not to be ended, the surgical process is continued (472). If the surgical process is to be ended, the system returns to step 402 to await a new accessory identification (474). If a user attempts to use a previously used accessory, the system activates the reader and transmits an encrypted destroy password to kill the tag embedded in the accessory so it cannot be re-used. For example, the tag may be "killed" by marking the tag as used in the RFID tag memory.

Figure 4A:
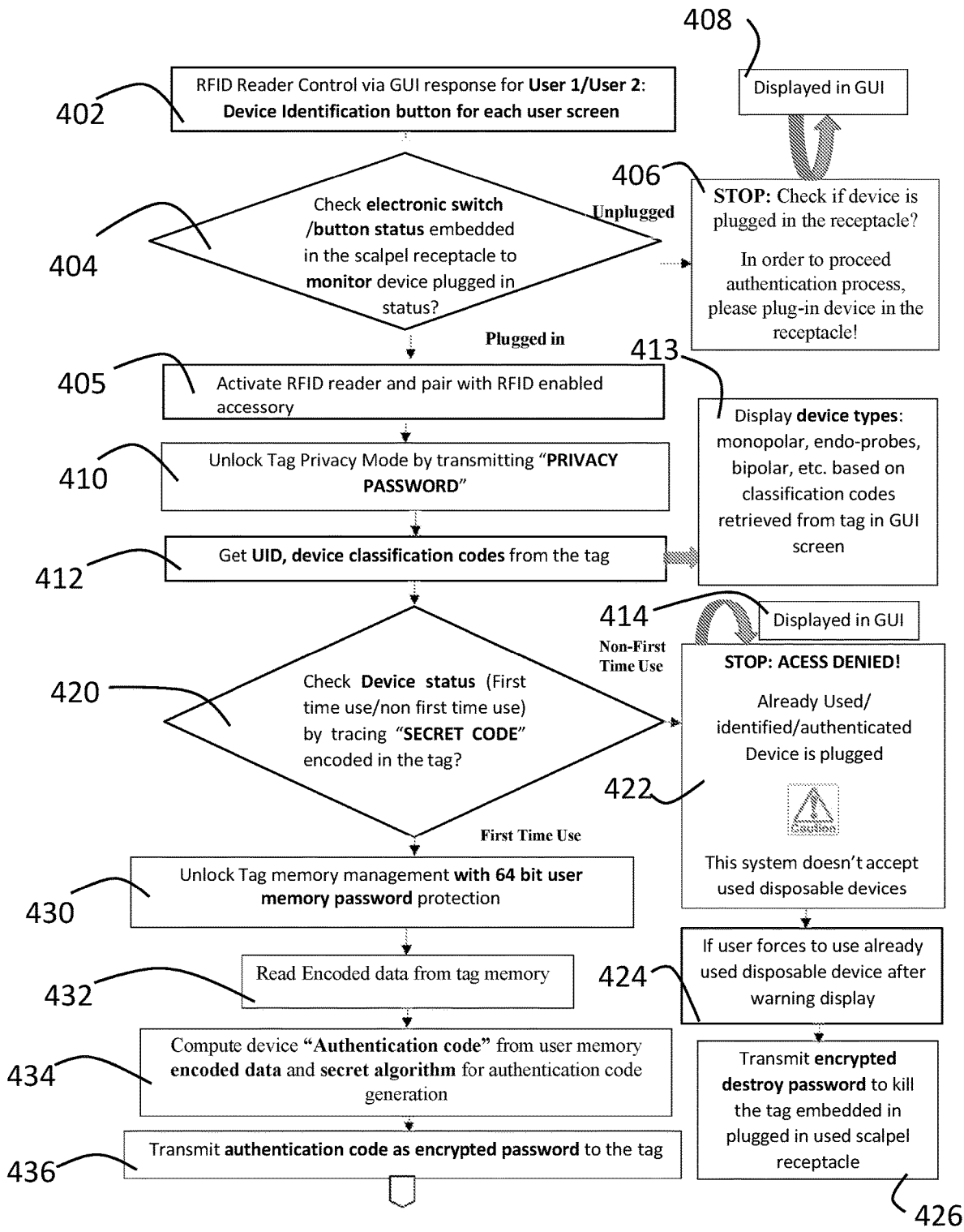
FIGS. 4A and 4B are flow diagrams of a system and method for RFID identification of electrosurgical attachments in accordance with a preferred embodiment of the present invention.
Figure 4B:
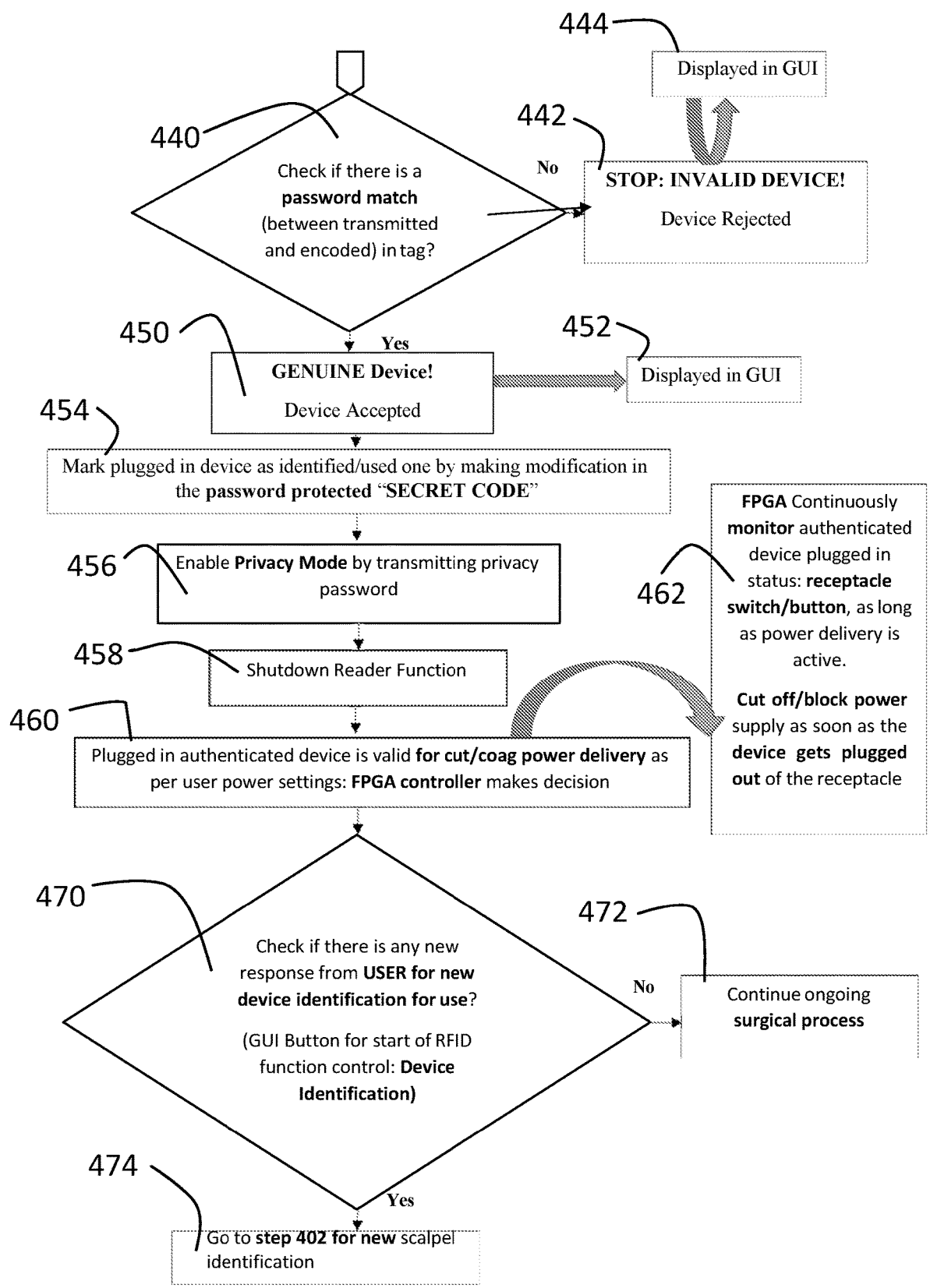
Figure 5:
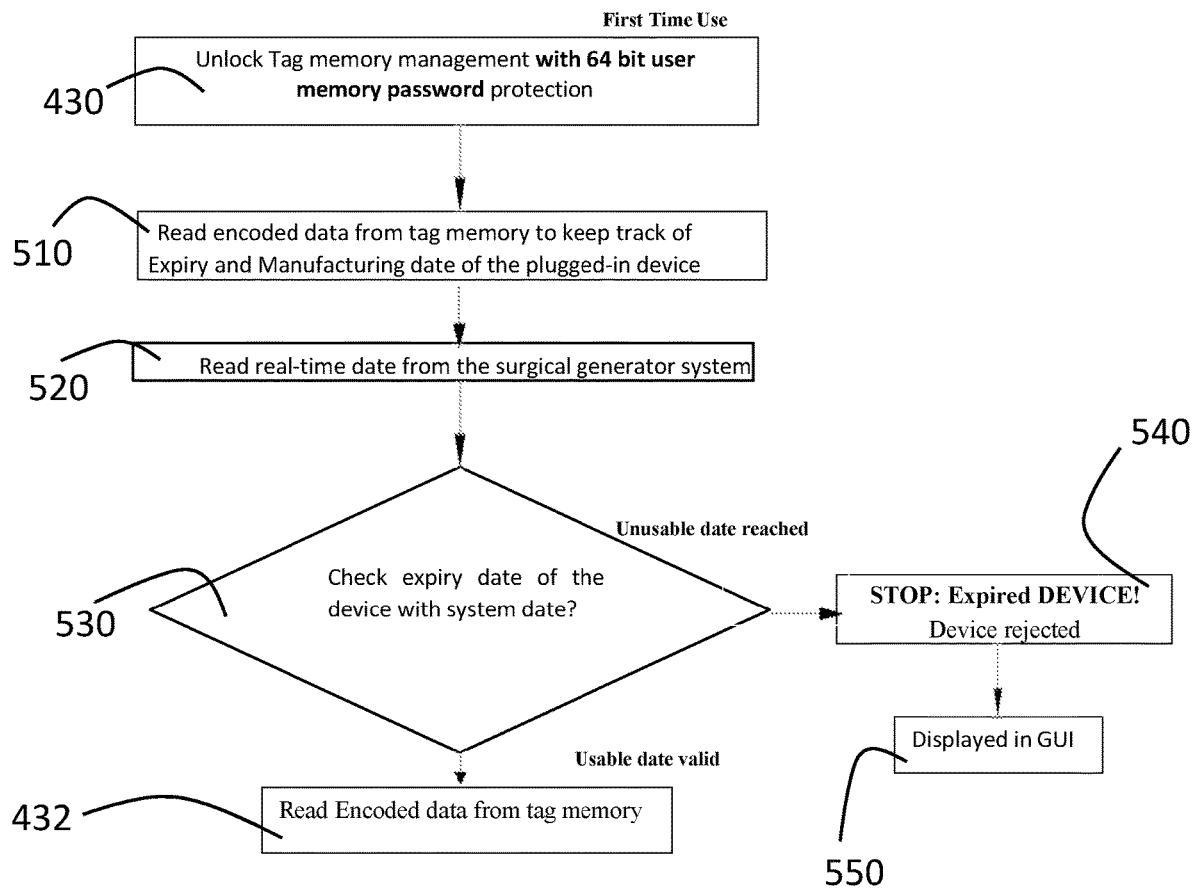
FIG. 5 is flow diagram of an alternate embodiment of a system and method for RFID identification of electrosurgical attachments in accordance with the present invention.

FIG. 5 illustrates an alternative embodiment in which several additional steps are inserted in between steps 430 and 432 in FIG. 4A to block use of expired surgical accessories with the system. In this alternate embodiment, after step 430 encoded data is read from the tag memory to keep track of the expiry and manufacturing date of the plugged-in device 510. Real-time date data is read from the surgical generator system 520. The system (e.g., a processor or CPU in the surgical generator system) checks whether the expiry date of the accessory read in step 510 is within (after) the real-time date read from the surgical generator system in step 520. The expiry date of the accessory is not within (i.e., is prior to) the real time date read from the surgical generator system, the device is deemed expired 540 and is rejected. An accessory rejection notice if displayed on the GUI 550. If the expiry date of the accessory is within the real-time date read from the surgical generator system, the system moves on to step 432.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A method for authentication of an accessory for an electrosurgical system comprising:
    initiating a device identification process through a user interface on an electrosurgical generator;
    automatically determining whether an electrosurgical accessory is plugged into a receptacle in said electrosurgical generator;
    activating an RFID reader connected to the electrosurgical generator in response to a determination that an accessory is plugged into a receptacle in said electrosurgical generator;
    transmitting from said generator through said RFID reader to an RFID tag in said accessory a privacy password;
    transmitting a unit identification code from said RFID tag through said RFID reader to said electrosurgical generator;
    displaying on a display in said electrosurgical generator a device type associated with said transmitted unit identification code;
    checking a first-time use status of said accessory by reading a status code protected by said privacy password from memory in said RFID tag;
    displaying a warning on a display in said electrosurgical generator if said status code read from said tag memory indicates that said accessory previously has been used;
    unlocking memory management of said RFID tag memory if said read status code indicates said accessory has not previously been used;
    reading encoded data from said RFID tag memory;
    computing in said electrosurgical generator a device authentication code from said encoded data read from said RFID tag memory;
    transmitting said computed authentication code from said electrosurgical generator to said RFID tag; and
    enabling said accessory in response to a match between said computed authentication code and an RFID tag authentication code stored in memory in said RFID tag.

2. A method for authentication of an accessory for an electrosurgical system according to claim 1, further comprising:
    wirelessly making changes in the RFID tag memory to indicate that the accessory has been used by modifying said password-protected status code in said RFID tag memory.

3. A method for authentication of an accessory for an electrosurgical system according to claim 1, further comprising:
    permanently disabling said RFID tag in the accessory wirelessly if a user attempts to re- use already used disposable surgical devices even after a displayed warning upon detection of a used in an accessory tag.

4. A method for authentication of an accessory for an electrosurgical system according to claim 1, further comprising:
    after said accessory is enabled displaying -on said user interface a message indicating said accessory is accepted for use.

5. A method for authentication of an accessory for an electrosurgical system according to claim 1, further comprising:
    in response to said unlocking of said RFID tag memory management, reading (encoded data from said RFID tag memory, said encoded data comprising data indicative of at least one of an accessory manufacture date and an accessory expiration date;
    comparing with a processor in said electrosurgical generator said at least one of an accessory manufacture date and an accessory expiration date to real-time data to determine if said accessory is expired;
    if said accessory is expired, displaying an expired message on a display; and
    if said accessory is not expired, proceeding to said step of reading encoded data from said RFID tag memory.

6. A method for authentication of an accessory for an electrosurgical system comprising:
    automatically determining with a processor in an electrosurgical generator whether an electrosurgical accessory is plugged into a receptacle in said electrosurgical generator by checking an electronic switch, button, or sensor in the receptacle;
    transmitting from said generator through an RFID reader to an RFID tag in said accessory a privacy password in response to said accessory being detected at plugged into a receptable in said electrosurgical generator;
    checking a first-time use status of said accessory by reading a status code protected by said privacy password from memory in said RFID tag;
    displaying a warning on a display in said electrosurgical generator if a read status code from said tag memory indicates that said accessory previously has been used;
    unlocking memory management of said RFID tag memory if said read status code indicates said accessory has not previously been used;
    reading encoded data from said RFID tag memory;
    computing in said electrosurgical generator a device authentication code from said encoded data read from said RFID tag memory;
    transmitting said computed authentication code from said electrosurgical generator to said RFID tag; and
    enabling said accessory in response to a match between said computed authentication code and an RFID tag authentication code stored in memory in said RFID tag.

7. A method for authentication of an accessory for an electrosurgical system according to claim 6, further comprising:

transmitting a unit identification code from said RFID tag through said RFID reader to said electrosurgical generator.

8. A method for authentication of an accessory for an electrosurgical system according to claim 7, further comprising:
displaying on a display in said electrosurgical generator a device type associated with said transmitted unit identification code.

9. A method for authentication of an accessory for an electrosurgical system according to claim 7, further comprising:
determining with a processor in said electrosurgical generator whether a device type associated with said unit identification code is compatible with a surgical procedure selected on a graphical user interface associated with said electrosurgical generator.

10. A method for authentication of an accessory for an electrosurgical system according to claim 6, further comprising:
wirelessly making changes in the RFID tag memory to indicate that the accessory has been used by modifying said password-protected status code in said RFID tag memory.

11. A method for authentication of an accessory for an electrosurgical system according to claim 6, further comprising:
in response to said unlocking of said RFID tag memory management, reading (encoded data from said RFID tag memory, said encoded data comprising data indicative of at least one of an accessory manufacture date and an accessory expiration date;
comparing with a processor in said electrosurgical generator said at least one of an accessory manufacture date and an accessory expiration date to real-time data to determine if said accessory is expired;
if said accessory is expired, displaying an expired message on a display; and
if said accessory is not expired, proceeding to said step of reading encoded data from said RFID tag memory.

* * * * *